(12) United States Patent
Bureiko et al.

(10) Patent No.: US 7,766,976 B2
(45) Date of Patent: Aug. 3, 2010

(54) POLYMER THICKENED HAIR COLOURING AND BLEACHING COMPOSITIONS

(75) Inventors: Andrei Sergeevich Bureiko, Sunningdale (GB); Ashok Saggi, Feltham (GB)

(73) Assignee: The Procter & Gamble Company, Cincinnati, OH (US)

( * ) Notice: Subject to any disclaimer, the term of this patent is extended or adjusted under 35 U.S.C. 154(b) by 177 days.

(21) Appl. No.: 11/291,666

(22) Filed: Dec. 1, 2005

(65) Prior Publication Data

US 2006/0117493 A1 Jun. 8, 2006

(30) Foreign Application Priority Data

Dec. 2, 2004 (EP) .................. 04257510

(51) Int. Cl.
*A61Q 5/08* (2006.01)
*A61Q 5/10* (2006.01)
(52) U.S. Cl. ............ 8/405; 8/406; 8/407; 8/408; 8/431; 8/620; 8/107; 8/111
(58) Field of Classification Search ........ 8/405, 8/406, 407, 408, 431, 619, 620, 107, 111
See application file for complete search history.

(56) References Cited

U.S. PATENT DOCUMENTS

| | | | |
|---|---|---|---|
| 3,726,967 | A | 4/1973 | Vorsatz et al. |
| 3,997,659 | A | 12/1976 | Knohl et al. |
| 4,566,875 | A | 1/1986 | Grollier |
| 4,776,855 | A | 10/1988 | Pohl |
| RE33,786 | E | 1/1992 | Pohl |
| 5,131,912 | A | 7/1992 | Ehara |
| 5,866,107 | A | 2/1999 | Schultz et al. |
| 6,071,504 | A * | 6/2000 | Kawai et al. ............ 424/70.12 |
| 6,540,791 | B1 * | 4/2003 | Dias .................. 8/111 |
| 6,821,302 | B2 * | 11/2004 | Au et al. ............... 8/405 |
| 7,044,986 | B2 | 5/2006 | Ogawa |
| 7,204,861 | B2 | 4/2007 | Marsh |
| 7,476,259 | B2 | 1/2009 | Bolton |
| 7,481,846 | B2 | 1/2009 | Marsh |
| 7,597,719 | B2 | 10/2009 | Bureiko |
| 2001/0033846 | A1 * | 10/2001 | Roulier et al. .......... 424/400 |
| 2002/0184717 | A9 * | 12/2002 | Cottard et al. ............ 8/405 |
| 2003/0051297 | A1 * | 3/2003 | Patel et al. ............. 8/405 |
| 2003/0077237 | A1 | 4/2003 | Legrand |
| 2004/0010865 | A1 | 1/2004 | Ogawa |
| 2004/0019980 | A1 | 2/2004 | Au |
| 2004/0060125 | A1 * | 4/2004 | Audouset ............... 8/405 |
| 2004/0083557 | A1 | 5/2004 | Au |
| 2004/0098814 | A1 | 5/2004 | Au |
| 2004/0098816 | A1 | 5/2004 | Au |
| 2004/0181883 | A1 | 9/2004 | Legrand |
| 2004/0237218 | A1 * | 12/2004 | Marsh et al. ............ 8/405 |
| 2006/0117493 | A1 | 6/2006 | Bureiko |
| 2006/0117494 | A1 | 6/2006 | Marsh |
| 2006/0117498 | A1 | 6/2006 | Bureiko |
| 2008/0010754 | A1 | 1/2008 | Bureiko |
| 2009/0297463 | A1 | 12/2009 | Bureiko |

FOREIGN PATENT DOCUMENTS

| | | | |
|---|---|---|---|
| EP | 1484047 | A | 12/2004 |
| JP | 60155108 | A2 | 8/1985 |
| JP | 63174917 | A2 | 7/1988 |
| JP | 01165514 | A2 | 6/1989 |
| JP | 03170413 | A2 | 7/1991 |
| JP | 06271435 | A2 | 9/1994 |
| JP | 07082123 | A2 | 3/1995 |
| JP | 08157345 | A2 | 6/1996 |
| JP | 09002925 | A2 | 1/1997 |
| JP | 10226630 | A2 | 8/1998 |
| JP | 11012140 | A2 | 1/1999 |
| JP | 11199454 | A2 | 7/1999 |
| JP | 2001206825 | A2 | 7/2001 |
| JP | 2001328926 | A2 | 11/2001 |
| JP | 2002173418 | A2 | 6/2002 |
| JP | 2002187826 | A2 | 7/2002 |
| JP | 2002193770 | A2 | 7/2002 |
| JP | 2002193772 | A2 | 7/2002 |
| JP | 2002338446 | A2 | 11/2002 |
| JP | 2002363048 | A2 | 12/2002 |
| JP | 2003512309 | T2 | 4/2003 |
| JP | 2004161707 | A2 | 6/2004 |
| JP | 2004224792 | A2 | 8/2004 |
| JP | 2004524333 | T2 | 8/2004 |
| JP | 2004524353 | T2 | 8/2004 |
| JP | 2005023023 | A2 | 1/2005 |
| JP | 2005194202 | A2 | 7/2005 |
| WO | WO-90/07529 | A | 7/1990 |
| WO | WO-01/28508 | | 4/2001 |
| WO | WO 01/28508 | A1 | 4/2001 |
| WO | WO 02/074272 | * | 9/2002 |

* cited by examiner

*Primary Examiner*—Lorna M Douyon
*Assistant Examiner*—Amina Khan
(74) *Attorney, Agent, or Firm*—Laura R. Grunzinger; Melissa G. Krasovec

(57) ABSTRACT

The present invention relates to hair coloring and hair bleaching compositions comprising a source of carbonate ions, at least one oxidizing agent and a specified polymer thickener wherein the composition is free of a source of radical scavengers. The compositions surprisingly provide improved hair colorant and bleaching compositions which deliver improved lift, lightening and color delivery whilst minimizing damage which are easy to manufacture and have long shelf life stability.

6 Claims, No Drawings

POLYMER THICKENED HAIR COLOURING AND BLEACHING COMPOSITIONS

FIELD OF THE INVENTION

The present invention relates to hair colourant and bleaching compositions.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex where they can then react with each other and suitable oxidising agents to form the end dye molecules. Due to the larger size of these resultant molecules they are unable to readily diffuse out of the hair during subsequent washing with water and/or detergents; hence delivering a consumer-desired permanency of colour. This reaction typically takes place in an aggressive environment at approximately pH 10 in the presence of an alkalizing agent and in the presence of an oxidizing agent. Moreover, the consumer repeats this process regularly in order to maintain the desired hair colour and shade and the intensity of colour and to ensure continual, even coverage of the hair including coverage of new hair growth.

The manufacturer of such products is also required to work within a large number of constraints. Since these products are being placed in direct contact with the consumers' skin, the potential exists for accidental contact with the eye or for ingestion (for example), which can occur during the dyeing process. Therefore, the formulation must meet rigorous safety requirements and not induce any allergic reactions. In addition to meeting these requirements, the products must also be optically and olfactory pleasing to the consumer. In particular, the products also need to meet certain physical parameters in order to ensure that the product can be easily applied to the hair by the consumer to provide the desired effect, without unintentional staining of the consumers' clothes, skin, particularly along the hair line, or other objects.

The manufacturer is also required to provide the hair colouring consumer a large range of different resulting colours. Some consumers may just wish to enhance the natural colour of the hair, whilst others may wish to cover grey or completely alter the hair colour to a different natural appearing hair colour or a 'synthetic' appearing hair colour. Consequently, the manufacturer may provide over twenty different formulations, of varying colours and shades, to address the range of consumer specific needs. These formulations have to be individually formulated and are typically complex formulae containing a mixture of different dye compounds. As a result the manufacture of such product ranges can be costly and complex.

However, despite the fact that commercial hair dyeing products have been available for many years, the products still exhibit a number of consumer-related deficiencies.

Typically permanent hair dye products will contain an alkali, typically a source of ammonia. This serves the purpose of swelling the hair allowing the entry of the dye precursor molecules into the hair and also improves the lightening effect of the oxidising agent, which is typically hydrogen peroxide. However, ammonia is also volatile and its associated odour is extremely unpleasant to the consumers' of such products, particularly as these hair dye products are used in close proximity to the nasal region. Hence, it would be highly desirable to provide an oxidative hair colouring and/or bleaching composition, which delivers the consumer required lightening level and colour, but which has reduced or eliminated the detectable ammonia odour.

In fact another deficiency area in current hair colouring products is the provision of hair colouring products which deliver the required hair lightening effect. Delivering the required level of lightening is particularly important in order to provide the full range of colour shades demanded by the consumer, especially for blonde shades and grey coverage. Such products pose particular difficulties to the manufacturer, as they usually require the use of high levels of oxidising agent and ammonia in order to deliver the required lightening effect. However, in additional to the problems associated with the presence of high levels of ammonia in these products, as discussed herein above, the presence of these high levels of ammonia and/or oxidizing agent also affect the condition of the hair and may in some cases induce mild skin irritation on the scalp. In particular, the hydrophilicity of the hair surface is increased during the colouring process, which alters the sensory perception of the hair and its overall manageability during and, immediately after colouring, and during the subsequent wash and styling cycles until the next colourant application. Hence, it would also be highly desirable to provide an oxidative hair colouring and/or bleaching composition which delivers the required lightening and/or colour without unnecessary hair damage.

A number of attempts have been described in the literature to address at least some of the above identified improvement areas. For example the use of carbonate has been described in the following hair colouring art. EP 435 012 describes hair-dyeing compositions, which require a short dyeing time, create little damage to hair, and no irritating odour after dyeing comprising a carbonate source, a non odour generating alkali hydrogen peroxide and a buffer solution. Similarly EP 1 106 166 describes hair dye compositions comprising ammonia, carbonate (other than ammonia salt), transition metal salt and chelating agent which do not give off an irritating odour, have low skin irritation and can change the hair colour into a lighter tone in a short time. WO01/28508 describes hair colouring formulations comprising oxidising agents and ammonia carbonate or carbamate which deliver improved bleaching and colouring with reduced odour and hair damage without the need for buffering agents, pH modifiers or hair swelling agents. JP01206825 describes a low pungent hair colouring composition comprising ammonia, ammonium salt and carbonate. US2004/0083557 describes hair colouring compositions comprising an oxidative hair dye precursor, a metal cyanate, an alkalizing agent and an oxidizing agent and preferably a metal bicarbonate salt in order to provide good colour lift and low odour.

WO04/014328 describes one step hair colouring compositions comprising peroxide oxidizing agents, specific oxidizing agents and at least one water soluble carbonate releasing salts which more effectively deliver colour wherein the composition is applied for a period of from 2 to 60 minutes. US2004/0098814 describes a method of permanently colouring hair whereby the hair is subjected to a number of consecutive short treatments whereby the treatment comprises a dye intermediate in a shampoo or conditioner base, a water soluble carbonate releasing salt and a water soluble ammonium salt. US2004/0098816 also describes a method for the gradual permanent colouring of hair which includes subjecting the hair to a number of treatments having a set time interval between them, wherein the treatment compositions comprise ammonium carbonate in combination with a chelant.

However it has now been found that the use of hydrogen peroxide and carbonate hair colourant systems, results in difficulties in manufacturing. This problem is particularly manifest for compositions which have high levels of peroxide and carbonate which are desirable to provide high levels of lift. Moreover in order to provide a product which the consumer can easily apply to the hair without dripping onto the skin, clothes or bathroom surfaces, hair colourant products are designed such that the composition has a certain required viscosity. This is either achieved by providing the dye composition and the oxidizing composition as so called thin-thin type liquid formulations which are thickened upon mixing or where at least one of the components, either the dye composition or the oxidizing composition, preferably the dye composition, is provided as a thickened formulation which thickens the total composition upon mixing.

Carbonate systems in the art herein above describe numerous materials suitable for thickening. However these materials have been found not to sufficiently thicken compositions comprising high levels of carbonate resulting in product instability or unsatisfactory viscosity. Hence it would be desirable to provide a hair colorant composition which incorporates high levels of carbonate without compromising the product stability or ease of manufacture.

Another particularly critical performance area for the consumer is the provision of the desired resultant colour and also the effective coverage of grey hair. Indeed, whilst the amount of grey hair to be coloured varies considerably from consumer to consumer, the resultant overall appearance of the coloured hair demanded by the consumer should be nearly identical for the naturally pigmented hair and the grey hair on head, with the added requirement that the initial uniform and even colour coverage is maintained during the post dyeing washing and drying cycle.

Hence, it would be further desirable to provide the consumer with a hair colourant, providing improved lift and lightening and improved colour delivery, uptake and durability and which is easy to manufacture, delivering the required viscosity and is shelf life stable.

It has now been surprisingly found that oxidative hair colouring compositions comprising an oxidising agent, a source of carbonate ions, a specific polymeric thickener as defined herein at pH 9.3 and below can be formulated as stable thickened systems. Moreover the compositions exhibit low odour and deliver a high level of lift and lightening equal to the currently utilised ammonia/peroxide systems, whilst reducing the concentration of peroxide and reducing the hair fibre damage. Moreover, the compositions of the present invention are compatible with current dyes and dye precursor systems and result in improved lift and lightening for blond shades, excellent dye deposition and colour and improved grey coverage.

SUMMARY OF THE INVENTION

The present invention relates to a hair colouring or bleaching composition comprising
i) at least about 0.2 mol/l of a source of carbonate, carbamate, hydrogencarbonate ions, or peroxymonocarbonate ions and mixtures thereof,
ii) at least one oxidizing agent and
iii) at least one polymeric thickener selected from associative polymers, non-associative polycarboxylic polymers, and mixtures thereof, wherein said composition has a pH of up to and including about 9.3 and wherein said composition is free of a source of radical scavengers.

A further embodiment of the present invention relates to a hair colouring or bleaching kit comprising
i) an individually packaged oxidizing component comprising at least one source of hydrogen peroxide
ii) an individually packaged liquid second component comprising
    a) at least one polymeric thickener selected from associative polymers, polysaccharides non-associative, polycarboxylic polymers, and mixtures thereof, and
    b) a source of carbonate ions, carbamate ions, hydrogencarbonate ions, and
    c) at least about 10% of a solvent, preferably water, wherein said kit is free of a source of radical scavengers and upon mixing said components comprises at least about 0.2 mol/l of a source of carbonate ions, carbamate ions, hydrogencarbonate ions or peroxymonocarbonate ions and mixtures thereof, except when said polymeric thickener is an associative polymer when said composition comprises at about least 0.4 mol/l of said source.

An alternative embodiment relates to a hair colouring or bleaching kit comprising
i) an individually packaged liquid oxidizing component comprising
    a) at least one source of hydrogen peroxide, and
    b) at least one polymeric thickener selected from associative polymers, polysaccharides, non-associative polycarboxylic polymers, and mixtures thereof, and
    c) at least about 10% by weight of a solvent, preferably, water,
ii) an individually packaged second component comprising a source of carbonate ions, carbamate ions or hydrogencarbonate ions and mixtures thereof wherein said kit is free of a source of radical scavengers and upon mixing said components comprises at least about 0.2 mol/l of a source of carbonate ions, carbamate ions, hydrogencarbonate ions, peroxymonocarbonate ions and mixtures thereof, except when said polymeric thickener is an associative polymer when said composition comprises at least about 0.4 mol/l of said source.

A further embodiment relates to a method of colouring or bleaching hair comprising the steps of applying a composition comprising at least about 0.2 mol/l of source of carbonate, carbamate, hydrogencarbonate ions or peroxymonocarbonate ions and mixture thereof, and at least one polymeric thickener selected from associative polymers, polysaccharides, non-associative cross-linked polycarboxylic polymers, and mixtures thereof, wherein said composition is free of radical scavenger, to the hair.

In a further aspect the present invention relates to a method of applying the compositions of the present invention to the hair and leaving the compositions on the hair for up to about 60 minutes, and subsequently rinsing the compositions from the hair.

Another aspect of the present invention relates to a method of sequential oxidative hair colouring or hair bleaching comprising the steps of at least two sequential oxidative hair colour or hair bleaching treatments wherein the time period between each treatment is from about 1 day to about 60 days, and wherein each treatment comprises the steps of providing a composition of the present invention, then applying said composition to the hair and retaining said composition on the hair for a time period of less than about 20 minutes and subsequently rinsing said composition from the hair.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by volume of the total composition and presented as number of moles of component(s) in one litre of the composition, or "mol/l". When more than one composition are used during a treatment, the total volume to be considered is the total volume of all the compositions applied on the hair simultaneously (i.e. the volume found "on head") unless otherwise specified.

Carbonate Ion Source

According to the present invention the compositions comprise at least 0.2 mol/l of source of carbonate ions or carbamate ions or hydrogencarbonate ions or peroxymonocarbonate ions or any mixture thereof. This amount can be achieved for example by addition of at least about 1.92% (volume percent) of ammonium carbonate (molecular weight equals to 96.09 g/mol) to the composition of invention or, for example, by addition of about 1.0% (volume percent) of Ammonium Carbonate and at least about 0.96% (volume percent) of Potassium Hydrogen Carbonate (molecular weight equals 100.12 g/mol). The compositions of the present invention preferably comprises from about 0.4 mol/l to about 2.0 mol/l, more preferably from about 0.5 mol/l to about 1.5 mol/l of the source of said ions.

It should also be understood that when the composition of the invention is used as a hair colouring or bleaching kit comprising and individually packaged oxidizing component and an individually packaged second component such as a bleaching or colouring component, the concentration of the source of the said ions will be increased in the said bleaching or colouring component proportionally to the mixing ratio of components in order to achieve the concentration of at least 0.2 mol/l (or 0.4 mol/l) upon mixing of the components to provide the composition applied to the hair.

Any source of these ions may be utilized. Suitable sources for use herein include sodium, potassium, lithium, calcium, magnesium, barium, ammonium salts of carbonate, carbamate and hydrogencarbonate ions and mixtures thereof such as sodium carbonate, sodium hydrogen carbonate, potassium carbonate, potassium hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrogencarbonate ions are sodium hydrogen carbonate, potassium hydrogen carbonate, ammonium carbamate and mixtures thereof.

In a particularly preferred embodiment of the present invention, the ammonium ion source and the carbonate ion sources are provided by a single source such as ammonium carbonate, ammonium hydrogen carbonate, ammonium carbamate or mixtures thereof.

Oxidizing Agent

The compositions according to the present invention thus form peroxymonocarbonate ions. These ions are typically formed in-situ from the reaction between a source of hydrogen peroxide and carbonate ion. Consequently, the compositions according to the present invention comprise or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and/or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions), persulphates and combinations thereof.

According to the present invention the compositions comprise from about 0.1% to about 10% by weight, preferably from about 1% to about 7% by weight, and most preferably from about 2% to about 5% by weight of an oxidizing agent.

Polymer Thickener

According to the present invention, the hair colouring and bleaching compositions comprise a polymer thickener, comprising at least one polymer selected from associative polymers, polysaccharides, non-associative polycarboxylic polymers, and mixtures thereof.

Those skilled in the art will recognize that polymer thickening systems usually provide thickening by chain entanglement, network formation or micro-gel swelling. These systems usually have gel appearance and feel and are thus strongly desirable.

However, polymer thickeners can be salted out by high level of carbonate salts, leading to viscosity loss. Further, osmotic swelling of micro-gel particles made of, for example, cross-linked polymers is suppressed by carbonate salt addition, also resulting in viscosity loss.

Even further, other components of typical colouring composition such as solvents and oxidative or pre-formed dyes, affect polymer properties and make selection of suitable polymers in carbonate systems particularly difficult. Further, in one of the embodiment of this invention, polymers have to be incorporated into a liquid composition i.e a composition comprising at least 10% by weight of a solvent such as water, together with carbonate salts, and provide shelf life stability of such liquid composition.

Surprisingly, it has now been found that by the required specific selection of the polymer thickener, thickening efficiency can be achieved. Without being bound by theory, it is believed that the polymer thickener described in this invention has sufficiently high molecular weight to resist salting-out by carbonate salts, or exhibits network formation via hydrophobic associative groups not affected by the presence of high concentrations of carbonate ions, or demonstrates sufficient osmotic swelling of micro-gel particles due to specific selection of polymer hydrophilic monomers, thus providing sufficient thickening.

According to the present invention the hair coloring or bleaching compositions and kits thereof comprise at least one polymeric thickener selected from associative polymers, polysaccharides, non-associative cross-linked polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Representative associative thickeners that may be used are associative polymers chosen from:
(i) nonionic amphiphilic polymers comprising at least one hydrophilic unit and at least one fatty-chain unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and
(iv) amphoteric amphiphilic polymers comprising at least one hydrophilic unit and at least one fatty-chain unit.

The nonionic amphiphilic polymers comprising at least one fatty chain and at least one hydrophilic unit may, for example, be chosen from:
(1) celluloses modified with groups comprising at least one fatty chain; for example: hydroxyethylcelluloses modified with groups comprising at least one fatty chain chosen from alkyl, alkenyl and alkylaryl groups;
(2) hydroxypropyl guars modified with groups comprising at least one fatty chain;
(3) polyether urethanes comprising at least one fatty chain, such as C8-C30 alkyl or alkenyl groups;
(4) copolymers of vinylpyrrolidone and of fatty-chain hydrophobic monomers;
(5) copolymers of C1-C6 alkyl acrylates or methacrylates and of amphiphilic monomers comprising at least one fatty chain;
(6) copolymers of hydrophilic acrylates or methacrylates and of hydrophobic monomers comprising at least one fatty chain.

The anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, chosen from units derived from acrylic acids, methacrylic acids and mixtures thereof, wherein the fatty-chain allyl ether unit corresponds to the monomer of formula below:

CH2=C(R1)CH2OB*n*R    (I)

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

The anionic amphiphilic polymers may further be chosen, for example, from those comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid. The hydrophilic unit of unsaturated olefinic carboxylic acid type corresponds to, for example, the monomer of formula (II) below:

CH2=C(R1)COOH    (II)

in which R1 is chosen from H, CH3, C2H5 and CH2COOH, i.e. acrylic acid, methacrylic, ethacrylic and itaconic acid units. And the hydrophobic unit of the type such as a (C8-C30) alkyl ester or (C8-C30) oxyethylenated alkyl ester of an unsaturated carboxylic acid corresponds to, for example, the monomer of formula (III) below:

CH2=C(R1)COOB*n*R2    (III)

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical.

Representative anionic amphiphilic polymers that can be used may further be cross-linked.

The crosslinking agent can be a monomer comprising a group (IV)

CH2=C<    (IV)

with at least one other polymerizable group whose unsaturated bonds are not conjugated with respect to one another. Mention may be made, for example, of polyallyl ethers such as polyallylsucrose and polyallyl pentaerythritol.

The cationic amphiphilic polymers used are, for example, chosen from quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Among amphoteric amphiphilic polymers comprising at least one hydrophilic unit and at least one fatty-chain unit, mention may be made, for example, of methacrylamidopropyltrimethylammonium chloride/acrylic acid/C8-C30 alkyl methacrylate copolymers, wherein the alkyl radical is, for example, a stearyl radical.

Preferable associative polymeric thickeners for use herein comprise at least one hydrophilic unit which is unsaturated carboxylic acid or its derivative, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Examples can be made of material sold under trade name ACULYN® 22 by the company Rohm & Haas, materials sold under trade names PERMULEN® TR1, CARBOPOL® 2020, CARBOPOL® Ultrez-21 by the company Noveon, and materials sold under the trade names STRUCTURE® 2001 and STRUCTURE® 3001 by the company National Starch. Another preferable associative polymer for use in the polymer thickening systems of the present invention include polyether polyurethane, for example materials sold under the trade name ACULYN® 44 and ACULYN® 46 by the company Rohm and Haas. Another preferable associative polymer for use herein is cellulose modified with groups comprising at least one C8-C30 fatty chain, such as the product NATROSOL® PLUS Grade 330 CS sold by the company Aqualon.

Non-associative cross-linked polycarboxylic polymers for use herein can be chosen, for example, from:
(i) cross-linked acrylic acid homopolymers;
(ii) copolymers of acrylic or (meth)acrylic acid and of C1-C6 alkyl acrylate or (meth)acrylate.

Preferable polymers are the products sold under the names Carbopol 980, 981, 954, 2984, 5984 by the company Noveon or the products sold under the names Synthalen M, Synthalen L and Synthalen K by the company 3V Sigma, or the product sold under the name Aculyn-33 by the company Rohm and Haas.

The polysaccharides for use herein are, for example, chosen from glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans and mixtures thereof.

For example, suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums—Polysaccharides and their Derivatives", edited by Roy L. Whistler, Second Edition, published by Academic Press Inc., the content of these three publications being entirely incorporated by reference.

The polysaccharide is preferably a bio-polysaccharide, particularly preferable are bio-polysaccharides selected from xanthan gum, gellan gum, welan gum, scleroglucan or succinoglycan, for example material sold under the name KELTROL® T by the company Kelco and the material sold by the name RHEOZAN® by the company Rhodia Chimie.

Another preferable polysaccharide is hydroxypropyl starch derivative, particularly preferable hydroxypropyl starch phosphate, for example the material sold under the name Structure XL® by the company National Starch.

pH

The compositions of the present invention have a pH up to and including about pH 9.3. Preferably, the compositions of the present invention have a pH of from about 9.3 to about 7.5, more preferably from about 9.3 to about 8.4 and most preferably from about 9.2 to about 8.5 and even more preferably about pH 9.0. Preferably, the compositions of the present invention are prepared such that prior to application to the hair fibres the pH of the composition is no greater than about pH 9.3. However, in another embodiment of the present invention the compositions may be formulated such that the pH is up to 9.3 during the time period of application of the composition to the hair fibres prior to removal therefrom. Preferably, the pH is up to about 9.3 for at least about 50% of the time period, preferably at least about 70%, most preferably at least about 80% of the time period of application of the composition to the hair. More preferably, the pH of the composition is up to about pH 9.3 within about 10 minutes, preferably within about 5 minutes of application to the hair fibres.

The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

Radical Scavenger

According to the present invention the compositions are typically free of a source of radical scavenger. The term free as used herein refers to compositions comprising less than 3%, preferably less than 2%, more preferably less than 1%, even more preferably less than 0.1% even more preferably less than 0.01% and even more preferably less than 0.001% and most preferably substantially free of a source of radical scavenger.

As used herein the term radical scavenger refers to compounds according to the general formula: (I): $R^1$—Y—C(H)$(R^3)$—$R^4$—$(C(H)(R^5)$—Y—$R^6)_n$ wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, 5$^{th}$ ed. (2001) at pages 368-375). Without being limited by theory, it is believed that substituents having sigma para values in the chosen ranges, when substituted onto $R^1$ and/or R2, may improve the compound's toxicological profile without unduly adding an unfavourable increase in molecular weight that may interfere with the molecule's ability to penetrate the hair shaft. Some preferred substituents and their Hammett Sigma Para values are shown below, in Table A. Additional substituents and their values are shown in March, at page 370.

TABLE A

| Substituent | $NH_2$ | OH | H | COO— | Cl | COOH | $CF_3$ |
|---|---|---|---|---|---|---|---|
| $\square_p$ | −0.57 | −0.38 | 0 | 0.11 | 0.24 | 0.44 | 0.53 |

Preferably the above defined radical scavengers have a pKa of more than 7 to prevent the protonation of the nitrogen.

Preferably the present invention further does not comprise radical scavengers according to the general formula (II):

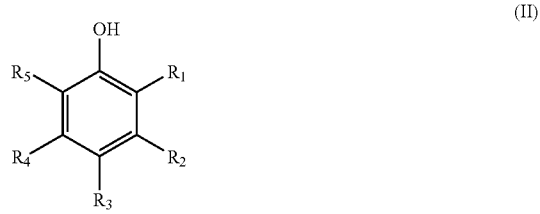

(II)

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy goup.

Preferably the present invention further also does not comprise radical scavengers according to those selected from group (III) benzylamine, imidazole, di-tert-butylhydroxytoluene, hydroquinone, guanine, pyrazine, piperidine, morpholine, methylmorpholine, 2methyoxyethylamine, and mixtures thereof.

Even more preferably the present invention does not comprise radical scavenger defined as a species that can react with a carbonate radical to convert the carbonate radical by a series of fast reactions to a less reactive species, i.e. a carbonate radical scavenger.

Whilst not being bound by theory, it is believed that the ability of the radical scavenger to convert the carbonate radical (as described hereinabove) is dependant upon the energy of the charge transfer reaction as shown below: (The calculation of the energy of the charge transfer reaction is detailed hereinafter.)

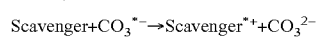

wherein the energy of the reaction is defined by:

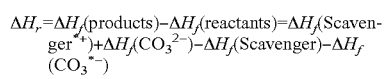

According to the present invention the composition do not comprise a radical scavenger having an energy of reaction of from about 0 kcal/mol to about 14 kcal/mol, preferably from about 1.5 kcal/mol to about 9 kcal/mol.

Additional Components

The compositions of the present invention may further comprise additional ingredients which include, but are not limited to, hair dyeing agents such as oxidative dye precursors, non-oxidative dyes, solvents, enzymes, surfactants, conditioning agents, carriers, antioxidants, stabilizers, chelants, perming actives, perfume, reducing agents (thiolactic acid), hair swelling agents and/or polymers. Some of these additional components are detailed hereafter.

Source of Alkalizing Agent

According to the present invention the composition may optionally comprise at least one source of alkalizing agent, preferably a source of ammonium ions and or ammonia. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof. Preferably, if present, the ammonium ions and carbonate ions are present in the composition at a weight ratio of from 3:1 to 1:10, preferably 2:1 to 1:5.

The compositions of the present invention may comprise from about 0.1% to about 10% by weight, preferably from about 0.5% to about 5%, most preferably from about 1% to about 3% of an alkalizing agent, preferably ammonium ions.

Hair Dyes

The hair compositions of the present invention are preferably hair colouring compositions which comprise oxidative dyeing compositions. Such compositions comprise oxidative hair dye precursors (also known as primary intermediates) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color. The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). Suitable dyes for use herein include: 1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-aminobenzene (p-AMINOPHENOL), 1-Hydroxynaphthalene (1-NAPHTHOL), 1,5-Dihydroxynaphthalene (1,5-NAPHTHALENEDIOL), 2,7-Dihydroxy-naphthalene (2,7-NAPHTHALENEDIOL), 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHENOL), 1,2,4-Trihydroxybenzene (1,2,4-TRIHYDROXY-BENZENE), 1-Phenyl-3-methylpyrazol-5-on (PHENYL METHYL PYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS(2-HYDROXY-ETHYL)-p-PHENYLENE-DIAMINE), 2,4,5,6-Tetraminopyrimidine (HC Red 16), 1-Hydroxy-3-methyl-4-aminobenzene (4-AMINO-m-CRESOL), 1-Hydroxy-2-amino-5-methylbenzene (6-AMINO-m-CRESOL), 1,3-Bis-(2,4-Diaminophenoxy)propane (1,3-BIS-(2,4-DIAMINO-PHENOXY)-PROPANE), 1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino)benzene (2-AMINO-4-HYDROXYETHYLAMINOANISOLE), 1-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylenedioxybenzene (HYDROXYETHYL-3,4-METHYLENE-DIOXY-ANILINE HCl), 2,6-Dihydroxy-3,4-dimethylpyridine (2,6-DIHYDROXY-3, 4DIMETHYLPYRIDINE), 3,5-Diamino-2,6-dimethoxypyridine (2,6-DIMETHOXY-3,5-PYRIDINEDIAMINE), 5,6-Dihydroxyindole (,DIHYDROXY-INDOLE), 4-Amino-2-aminomethylphenol (2-AMINOETHYL-p-AMINO-PHENOL HCl), 2,4-Diamino-5-methylphenetol (2,4-DIAMINO-5-METHYL-PHENETOLE HCl), 2,4-Diamino-5-(2'-hydroxyethyloxy) toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl)benzene (HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL), 6-Hydroxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5,2-phenyl-3H-pyrazole-3-one, 2-Amino-3-hydroxypyridine (2-AMINO-3-HYDROXYPYRIDINE), 5-Amino-salicylic acid, 1-Methyl-2,6-bis(2-hydroxy-ethylamino)benzene (2,6-HYDROXYETHYLAMINOTOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHENYLENEDIAMINE), 5,6-Dihydroxyindoline (DIHYDROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYYETHYL-4,5-DIAMINOPYRAZOLE SULPHATE). These can be used in the molecular form or in the form of peroxide-compatible salts.

The hair colouring compositions of the present invention may also include non oxidative hair dyes i.e. direct dyes which may be used alone or in combination with the above described oxidative dyes. Suitable direct dyes include azo or anthraquinone dyes and nitro derivatives of the benzene series and mixtures thereof. Such direct dyes are particularly useful to deliver shade modification or highlights. Particularly preferred are Basic Red 51, Basic Orange 31, Basic Yellow 87 and mixtures thereof.

The hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Surfactants

The compositions according to the present invention may further comprise one or more surfactants. Surfactants suitable for use herein generally have a lipophilic chain length of from about 8 to about 30 carbon atoms and can be selected from anionic, nonionic, amphoteric and cationic surfactants and mixtures thereof. Preferred surfactants include non-ionic surfactants comprising one or more polyethyleneoxide chain, for example polyoxyethylene alkyl ethers or polyethyleneglycol fatty acid esters. Another preferred surfactants are alkyl ether sulphates or alkyl ether phosphates, where particularly preferable are alkyl ether phosphates having 1-20, preferably 1-10 and most preferably 1-5 ethylene oxide units.

Any combination of surfactants can be used. Moreover, surfactants may form various micelle and liquid crystalline phases in the composition. Preferably, the surfactants will form a so-called lamellar gel network phase. The surfactants will generally be used at levels of from about 0.05% to about 30% by weight of the composition, preferably of from about 0.1% to about 15%, more preferably of from about 0.2% to about 10%.

Conditioning Agent

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Particularly useful conditioning materials are cationic polymers and silicones. Conditioners of cationic polymer type may be chosen from those already known by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethyiphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betain groups. The silicone can either be used as a neat fluid or in the form of an pre-formed emulsion.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation issues may arise.

Opacifying Agents

Suitable opacifiers may be selected from fatty alcohols, fatty acids, fatty amide derivatives, fatty esters of ethylene glycol and fatty acids of glycerol.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol. Finally, the compositions according to the present invention are thus typically provided as an aqueous composition. The compositions of the present invention comprise from 10%, preferably 20%, more preferably 30%, most preferably 50% by weight of a solvent.

Method of Use

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, a dye component (also called "dye cream" for emulsions or gels or "dye liquid" for solutions) comprising the oxidative dye, precursors and alkalizing agent which is typically ammonia in a suitable carrier, and; a hydrogen peroxide component (also called "hydrogen peroxide cream" for emulsions or gels or "hydrogen peroxide liquid" for solutions) comprising the oxidizing agent (usually hydrogen peroxide). The consumer mixes the dye component and hydrogen peroxide component together immediately before use and applies it onto the hair.

Similarly, bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

After working the mixture for a few minutes (to insure uniform application to all of the hair), the oxidative dye composition is allowed to remain on the hair for an amount sufficient for the dyeing to take place (usually from about 2 to 60 minutes, typically about 30 to 45 minutes). The consumer then rinses his/her hair thoroughly with tap water and allows it to dry. It is observed that the hair has changed from its original colour to the desired colour.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers.

For hair dye compositions the polymer thickener may be comprised within the dye component, or the hydrogen peroxide component or both components. The resultant hair colouring or bleaching compositions according to the present invention thus have a viscosity of from 1000 to 60000 cPs, preferably from 2000 to 30000 cPs and most preferably from 3000 to 25000 cPs. Moreover prior to mixing the hair dye component (component two) may have viscosity of less than 1000 cPs, such composition is ofter referred as "thin-thin" or "liquid" colorant. The viscosity of the resultant mixture of oxidative and dye components i) and ii) in other words the hair colouring or bleaching composition is from 1000 to 60000 cPs, preferably from 2000 to 30000, more preferably form 3000 to 25000 cPs. Viscosity is measured using Brookfield viscometers with cone and plate attachment. For viscosities in the range of 0-12000 cPs the Brookfield DV-11 viscometer with S42 plate is used. 2 ml sample of the composition is equilibrated at 26.7° C. for three minutes before the readings are taken at 1 rpm. For viscosities in the range of 12,000-50,000 cPs the Brookfield DV-1 viscometer with S52 plate is used. 0.5 ml sample of the composition is equilibrated for 1 minute at 26.7° C. before the readings are taken at 1 rpm.

The present invention also includes embodiments wherein the method of colouring or bleaching hair comprises applying a composition comprising at least one oxidising agent, at least one source of carbonate, carbamate, or hydrogen carbonate ions and mixtures thereof, and a polymer thickening system as defined herein free of radical scavengers, the composition having a pH of up to about 9.3, for at least about 50% of the time period the composition is applied to the hair.

According to the present invention the methods of colouring or bleaching hair also comprise embodiments whereby the composition is applied to the hair and preferably the mixture is worked for a few minutes (to insure uniform application to all of the hair). The composition is then allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual. This method provides additional convenience to consumer by permitting faster colouring or bleaching application.

According to an alternative embodiment of the present invention, the method of colouring and or bleaching the hair is a sequential oxidative hair colouring or hair bleaching method comprising the steps of at least two sequential oxidative hair colour or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes. This method allows consumer to perform colouring or bleaching process in a way similar to conventional hair washing or conditioning process.

The kits described hereinabove are well known in the art and the composition in each container can be manufactured utilizing any one of the standard approaches. For example, polymer is added to cold water with strong agitation (strong agitation is not required if polymer supplied as emulsion or suspension) and then mixed for about 1 hour with reduced agitation and optional heating to provide full polymer dissolution or dispersion or swelling. This polymer premix is then mixed cold with remaining amounts of water, other optional components and oxidizing agent or a source of carbonate, carbamate or hydrogencarbonate ions, thus forming first or second part of the above described bleaching or colouring kit.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aesrosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

EXAMPLES

The following examples illustrate oxidative dye compositions according to the present invention. It is understood that the examples and embodiments described herein are for illustrative purposes only and that various modifications or changes in light thereof will be suggested to one skilled in the art without departing from the scope of the present invention.

Examples 1-10 (Mixed Compositions)

| Ingredient | Formulation | | | | | | | | | | |
| --- | --- | --- | --- | --- | --- | --- | --- | --- | --- | --- | --- |
| | 1 | 2 | 3 | 4 | 5 | 6 | 7 | 8 | 9 | 10 | 11 |
| Ammonium Carbonate | 4.0 | — | 2.0 | — | — | — | — | 5.0 | 3.0 | — | — |
| Ammonium Hydrogen Carbonate | — | 1.0 | — | — | 2.5 | 4.0 | 2.0 | — | — | 4.0 | 1.0 |
| Ammonium Carbamate | — | 1.0 | — | — | 2.5 | 4.0 | 2.0 | — | — | 4.0 | 1.0 |
| Potassium Hydrogen Carbonate | — | — | 2.0 | 5.0 | — | — | — | — | 1.5 | — | — |
| | — | — | 5 | — | — | — | — | — | — | — | — |
| Acrylates Steareth-20 Methacrylate Copolymer (Aculyn ® 22) | 8.0 | — | 1.0 | — | — | — | — | — | — | — | — |
| Carbomer (Crabopol 980 ®) | — | 2.0 | — | — | — | — | — | — | — | — | 2.0 |
| Acrylates Copolymer (Aculyn ® 33A) | — | — | 4.0 | — | — | — | — | — | — | — | — |
| PEG-150/Decyl Alcohol/SMDI Copolymer (Aculyn ® 44) | — | — | — | 4.0 | — | — | — | — | — | — | — |

-continued

| Ingredient | 1 | 2 | 3 | 4 | 5 | 6 | 7 | 8 | 9 | 10 | 11 |
|---|---|---|---|---|---|---|---|---|---|---|---|
| Succinoglycan (Rheozan ®) | — | — | — | — | 1.0 | — | — | — | — | — | — |
| Xanthan gum | — | — | — | — | — | 1.5 | — | — | — | — | — |
| Acrylates/Steareth-20 Itaconate Copolymer (Structure ® 2001) | — | — | — | — | — | — | 2.0 | — | — | — | — |
| Acrylates/C10-30 Alkyl Acrylate Copolymer (Carbpol 2020 ®) | — | — | — | — | — | — | — | 2.0 | — | — | — |
| Cetyl Hydroxyethylcellulose (Natrosol ® Plus CS) | — | — | — | — | — | — | — | — | 1.5 | — | — |
| Hydroxypropyl Starch Phosphate (Structure XL ®) | — | — | — | — | — | — | — | — | — | 2.0 | — |
| Crodafos ® CES (Cetearyl alcohol, di-cetyl phosphate & ceteth-10 phosphate) | — | — | 2.5 | — | — | — | — | — | — | — | — |
| Crodafos ® S2A (Ceteth-2 phosphate) | 0.3 | — | — | — | — | — | — | — | — | — | — |
| Ceteareth-25 | — | — | — | 0.5 | 0.25 | — | 0.5 | 0.5 | 0.5 | 0.5 | — |
| Cetyl Alcohol | 0.3 | — | — | 1.0 | 0.5 | — | 1.0 | 1.0 | 1.0 | 1.0 | — |
| Stearyl Alcohol | 0.3 | — | — | 1.0 | 0.5 | — | 1.0 | 1.0 | 1.0 | 1.0 | — |
| Sodium sulphite | 0.1 | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 | 0.1 |
| EDTA(tetrasodium salt) | 0.1 | 0.1 | 0.1 | 0.1 | 0.1 | 0.1 | 0.1 | 0.1 | 0.1 | 0.1 | 0.1 |
| p-phenylene diamine | 0.8 | — | 0.6 | 0.1 | 0.8 | — | 0.6 | 0.1 | 0.8 | — | — |
| p-amino phenol | — | 0.3 | — | 0.4 | — | 0.3 | — | 0.4 | — | 0.3 | 0.3 |
| 2,5-diaminotoluene sulphate | — | 0.1 | 0.2 | — | — | 0.1 | 0.2 | — | — | 0.1 | 0.1 |
| m-aminophenol | 0.2 | — | 0.1 | — | 0.2 | — | 0.1 | — | 0.2 | — | — |
| Resorcinol | — | 0.5 | — | 0.4 | — | 0.5 | — | 0.4 | — | 0.5 | 0.5 |
| napthol | 0.03 | — | 0.2 | — | 0.03 | — | 0.2 | — | 0.03 | — | — |
| 4-amino-2-hydroxy toluene | — | 0.2 | — | 0.3 | — | 0.2 | — | 0.3 | — | 0.2 | 0.2 |
| Phenyl methyl pyrazalone | 0.2 | — | — | — | — | 0.1 | — | — | — | — | — |
| 1-hydroxyethyl-4,5-diamino pyrazole sulphate | 0.3 | — | — | — | — | 0.2 | — | — | — | — | — |
| Basic red 51 | — | 0.1 | — | — | — | — | 0.2 | — | — | — | 0.1 |
| Basic yellow 87 | — | 0.2 | — | — | — | — | 0.3 | — | — | — | 0.2 |
| Hydrogen Peroxide (35% active) | 8.6 | 8.6 | 8.6 | 13..0 | 13.0 | 13.0 | 17.0 | 10.7 | 10.7 | 10.7 | 4.0 |
| Polyquaternium-22 (Merquat ® 295) | — | — | — | — | 0.5 | — | — | — | — | — | — |
| Polyquaternium-37 & Mineral oil (Salcare ® SC95) | — | — | — | — | 0.1 | — | — | — | 0.5 | — | — |
| Amodimethicone (DCAP 6087) | — | — | — | — | — | — | — | — | — | 1.0 | — |
| Propylene Glycol | 4.0 | 3.0 | 3.0 | 4.0 | 3.5 | 3.0 | 4.0 | 4.0 | 3.0 | 3.0 | 3.0 |
| pH adjust to pH 9.0 | qs | qs | qs | qs | qs | qs | qs | qs | qs | qs | qs |
| Water | qs | qs | qs | qs | qs | qs | qs | qs | qs | qs | qs |

The viscosity of these compositions are within the range of from 1000 to 60000 cPs.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are the scope of this invention.

What is claimed is:

1. A solid hair coloring or bleaching composition comprising:
    i) at least one solid source of sodium percarbonate ions,
    ii) at least one solid source of ammonium sulfate, and
    iii) at least one solid, acrylates/steareth-20 Itaconate copolymer thickener having a dispersion viscosity before neutralization of less than about 10,000 cP at 20 rpm at a concentration in water of about 3% to about 5%;
    wherein upon admixture with water said composition generates peroxymonocarbonate ions and has a pH of from about 7.5 to about 9.5.

2. A solid hair coloring or bleaching composition according to claim 1, wherein said acrylates/steareth-20 Itaconate copolymer is a C10 to C30 alkyl acrylate steareth-20 Itaconate copolymer.

3. A solid hair coloring or bleaching composition according to claim 1, wherein said composition further comprises at least one oxidative dye, at least one direct dye, or combinations thereof.

4. A solid hair coloring or bleaching composition according to claim 1, wherein said composition further comprises a radical scavenger.

5. A solid hair coloring or bleaching composition according to claim 1, wherein said composition further comprises a chelating agent.

6. A method of treating hair comprising the steps of:
a. mixing a solid hair coloring or bleaching composition comprising i) at least one solid source of sodium percarbonate ions, at least one solid source of ammonium sulfate ions, and iii) at least one solid, acrylates/steareth-20 Itaconate copolymer thickener having a dispersion viscosity before neutralization of less than about 10,000 cP at 20 rpm at a concentration in water of about 3% to about 5% with water, wherein upon admixture with water said composition generates peroxymonocarbonate ions and has a pH of from about 7.5 to about 9.5.
b. applying said mixture to the hair, and
c. rinsing said mixture from the hair.

* * * * *